United States Patent
Beyar et al.

(10) Patent No.: US 7,615,042 B2
(45) Date of Patent: Nov. 10, 2009

(54) TRANSMISSION FOR A REMOTE CATHETERIZATION SYSTEM

(75) Inventors: Rafael Beyar, Haifa (IL); Tal Wenderow, Haifa (IL); Doron Linder, Haifa (IL); Eyal Zilberberg, Beit Halevi (IL)

(73) Assignee: Corindus Ltd., Haifa (IL)

( * ) Notice: Subject to any disclaimer, the term of this patent is extended or adjusted under 35 U.S.C. 154(b) by 80 days.

(21) Appl. No.: 10/561,147

(22) PCT Filed: May 10, 2005

(86) PCT No.: PCT/IL2005/000497

§ 371 (c)(1),
(2), (4) Date: Jun. 9, 2006

(87) PCT Pub. No.: WO2005/117596

PCT Pub. Date: Dec. 15, 2005

(65) Prior Publication Data

US 2006/0229587 A1   Oct. 12, 2006

(30) Foreign Application Priority Data

Jun. 3, 2004   (IL) .......... 162318

(51) Int. Cl.
*A61M 31/00*   (2006.01)
(52) U.S. Cl. .......... 604/510; 604/156; 604/528; 604/164.12; 604/165.02; 600/106; 600/137
(58) Field of Classification Search .......... 604/510, 604/582, 95.01, 156, 500, 523, 528, 164.12, 604/165.02; 600/106, 137, 101, 103, 114, 600/424; 74/425; 290/1 C; 310/114, 99
See application file for complete search history.

(56) References Cited

U.S. PATENT DOCUMENTS

| 5,377,678 | A | 1/1995 | Dumoulin et al. |
| 5,492,131 | A | 2/1996 | Galel |
| 6,171,234 | B1* | 1/2001 | White et al. .......... 600/102 |
| 6,726,675 | B1* | 4/2004 | Beyar .......... 604/510 |
| 2003/0176770 | A1* | 9/2003 | Merril et al. .......... 600/118 |
| 2004/0254566 | A1* | 12/2004 | Plicchi et al. .......... 606/1 |

FOREIGN PATENT DOCUMENTS

| EP | 0 331 944 A1 | 9/1989 |
| EP | 0 970 663 A1 | 1/2000 |
| EP | 1 442 720 A1 | 8/2004 |

OTHER PUBLICATIONS

Supplementary Partial European Search Report for Application Number EP 05 73 8429, dated Feb. 20, 2008, 4 pages.
PCT Written Opinion of the International Searching Authority for Application Number PCT/IL05/00497, dated May 19, 2006, 3 pages.
WIPO PCT International Search Report for Application Number PCT/IL05/00497, dated Dec. 15, 2005, 2 pages.

* cited by examiner

*Primary Examiner*—Nicholas D Lucchesi
*Assistant Examiner*—Quynh-Nhu H Vu
(74) *Attorney, Agent, or Firm*—Foley & Lardner LLP

(57) ABSTRACT

An apparatus for imparting motion from at least one of a plurality of motion sources into linear, rotary, or combined linear and rotary motion of an elongated device, the apparatus comprising a transmission for translating the motion to linear or rotary motion of the elongated device.

20 Claims, 5 Drawing Sheets

TRANSMISSION FOR A REMOTE CATHETERIZATION SYSTEM

FIELD OF THE INVENTION

The present invention relates generally to invasive medical probes and methods, and specifically to intravascular catheterization and catheterization techniques.

BACKGROUND OF THE INVENTION

Catheters are used for many medical procedures, including inserting a guide wire, delivering a stent, and delivering and inflating a balloon.

Catheterization procedures are very commonly performed for diagnosis and treatment of diseases of the heart and vascular system. The catheterization procedure is generally initiated by inserting a guide wire into a blood vessel in the patient's body. The guide wire is then guided to the desired location, most commonly in one of the heart vessels or elsewhere in the vascular system. At this point the catheter is slid over the guide wire into the blood vessel and/or heart. Once the catheter is in the desired position, the guide wire can then be removed, leaving the catheter in location. Alternatively, in some procedures, the catheter is inserted without using a guide wire. The catheter may be used to pass ancillary devices into the body, such as an angioplasty balloon, or to perform other diagnostic or therapeutic procedures.

Thus, at the present time the guidance of catheters and other medical devices in body lumens and cavities is still most often accomplished by providing a bent tip on the device or using a guide wire with a bent tip.

To insert a catheter manually, the physician applies torque and axial push force on the proximal end of a guide wire to effect tip direction and axial advancement at the distal end. However, it is difficult to control the distal tip of the catheter from the proximal end. Although these navigation techniques are effective, they are tedious, require extraordinary skill, and result in long medical procedures that fatigue the user.

Furthermore, to facilitate the guide wire insertion and the subsequent catheter application, the physician generally performs the procedure with the assistance of a fluoroscope, as is well known in the art. The fluoroscope produces a real-time image showing the continued progress of the guide wire, or the catheter, through the patient's body.

The fluoroscope generates a high level of X-ray radiation, which poses a significant danger to medical personnel exposed thereto, as is well known in the art. In order to provide protection from radiation exposure, the attending medical personnel generally wear a heavy, cumbersome protective lead garment which covers the entire body and neck, or use various lead shields including transparent glass face and eye shields. The use of fluoroscopy in the catheterization lab presents safety concerns for training, monitoring, and record keeping among the catheterization lab staff. The staff constantly monitors the radiation dosage that each member receives.

One solution for these problems is proposed by U.S. Pat. No. 6,522,909 (2003) Garibaldi, et al, "METHOD AND APPARATUS FOR MAGNETICALLY CONTROLLING CATHETERS IN BODY LUMENS AND CAVITIES", which provides an apparatus for navigating a magnet-tipped medical device through the body including a magnet system for applying a magnetic field to the magnet-tipped distal end of the medical device to orient the distal end of the medical device; a computer for controlling the magnet system to generate a specified magnetic field in the body part; first and second imaging devices connected to the computer, for providing bi-planar images of the body part through which the medical device is being navigated; first and second displays for displaying the images from the image devices; and an input device for inputting points identifying the desired path of the medical device on each of the displays. The computer is programmed to determine the magnetic field necessary to control orient the medical device on the path input on the displays.

However, U.S. Pat. No. 6,522,909 requires expensive and bulky equipment.

U.S. Pat. No. 5,779,623, POSITIONER FOR MEDICAL INSTRUMENTS (1998) Bonnell, features a remote-controlled device for selectively positioning a medical instrument within a predetermined region of space. The remote-controlled device has a motor which provides mechanical energy to the remote-controlled device, a driver that is coupled to the motor and that has a predetermined relationship with the motor. The driver physically engages the medical instrument and converts the mechanical energy into controlled motion of the medical instrument. The remote-controlled device receives control signals from a remote location that direct the motor to supply a predetermined amount of mechanical energy, whereby the driver, with the predetermined relationship with the motor, selectively positions the medical instrument within the region of space.

However, U.S. Pat. No. 5,779,623 does not provide rotational movement of the medical instrument, nor position feedback, nor a fast method for inserting and removing the instrument.

U.S. Pat. No. 6,726,675 REMOTE CONTROL CATHETERIZATION (2004), Dalia Beyar, describes a remote control catheterization system including a propelling device, which controllably inserts a flexible, elongate probe into the body of a patient. A control unit, in communication with the propelling device, includes user controls which are operated by a user of the system remote from the patient to control insertion of the probe into the body by the propelling device.

It is an object of some aspects of U.S. Pat. No. 6,726,675 to provide an apparatus and methods of catheterization that allow medical personnel to be distanced from the vicinity of the fluoroscope and its resultant radiation, thereby reducing radiation exposure of the personnel. It is a further object of some aspects of the U.S. Pat. No. 6,726,675 invention to provide a mechanism for remote control performance of catheterization procedures.

The present invention is intended to provide a transmission mechanism for a remote catheterization system, such as that provided in U.S. Pat. No. 6,726,675.

In a preferred embodiment of the present invention, the transmission is a mechanical assembly that holds a slender and greatly elongated solid medical component, such as a catheterization guide wire, between two pressure rollers. Linear motion of the guide wire is accomplished by motorized rotation of the rollers on their axes. Rotational motion of the guide wire is accomplished by motorized rotation of the assembly, which holds the rollers and the guide wire, around the guide wire's linear axis. Movement combining advance and rotation can be accomplished as well.

In summary, it is a main object of the present invention to provide a mechanical transmission for movement of a guide wire in a remote control catheterization system, with the following several objects and advantages:

Translates motor force into linear and rotational motion of the guide wire or other slender and greatly elongated solid medical component.

Can perform both linear and rotational motion simultaneously is simple and mechanically reliable provides two ways to mount guide wire in transmission: end insertion and side insertion In end insertion, the guide wire is fed into the transmission along the guide wire's longitudinal axis until the desired point on the guide wire is reached. In side insertion, a slot in the transmission enables the guide wire to be inserted directly at the desired point, with no need for feeding. The same principles apply when removing the guide wire from the transmission.

Still further objects and advantages will become apparent from a consideration of the ensuing description and drawings.

BRIEF DESCRIPTION OF THE INVENTION

There is thus provided, in accordance with some preferred embodiments of the present invention, an apparatus for imparting motion from at least one of a plurality of motion sources into linear, rotary, or combined linear and rotary motion of an elongated device, the apparatus comprising:

a transmission for translating the motion to linear or rotary motion of the elongated device.

Furthermore, in accordance with some preferred embodiments of the present invention, the external motion source is a motor.

Furthermore, in accordance with some preferred embodiments of the present invention, the apparatus further comprises:

a controller electrically connected via drive circuitry to the motor and receiving positioning commands from an individual or machine;

a position feedback sensor measuring movement of the drive mechanism;

wherein motion of the elongated device is controlled by a closed control loop comprising the controller driving the motor and the sensor providing feedback about the elongated device motion to the controller.

Furthermore, in accordance with some preferred embodiments of the present invention, the elongated device is a medical device.

Furthermore, in accordance with some preferred embodiments of the present invention, the elongated device is a guide wire.

Furthermore, in accordance with some preferred embodiments of the present invention, the elongated device is a catheter.

Furthermore, in accordance with some preferred embodiments of the present invention, there is provided a transmission apparatus for imparting linear, rotary, or combined linear and rotary motion to an elongated device, the apparatus comprising:

a first main gear rotationally attached to a support and capable of being driven by a first drive;

a second main gear coaxially and rotationally attached to the first main gear, the second main gear geared to a roller drive gear and capable of being driven by a second drive;

a linear drive in which the elongated device may be engaged along an axis of the elongated device's rotation, the linear drive coupled to the first main gear, such that when the first main gear is rotated, the elongated device is rotated about the elongated device's axis of rotation, the linear drive being geared to the roller drive gear, such that when the second main gear is rotated the linear drive imparts linear motion to the elongated device.

Furthermore, in accordance with some preferred embodiments of the present invention, the first drive and the second drive transmit power to the first main gear and the second main gear respectively via drive screws.

Furthermore, in accordance with some preferred embodiments of the present invention, the first drive and the second drive are motors.

Furthermore, in accordance with some preferred embodiments of the present invention, the first main gear and the second main gear are each provided with a slot to enable lateral insertion or removal of the elongated device.

Furthermore, in accordance with some preferred embodiments of the present invention, the first drive and the second drive are provided with a position tracking mechanism so as to allow automated alignment of the slots for insertion or removal of the elongated device.

Furthermore, in accordance with some preferred embodiments of the present invention, the linear drive comprises two geared rollers that are geared to the second main gear.

Furthermore, in accordance with some preferred embodiments of the present invention, the two geared rollers resiliently grip the elongated device, and may be separated in order to insert or remove the elongated device.

Furthermore, in accordance with some preferred embodiments of the present invention, a first position sensor measures the position of the first drive and a second position sensor measures the position of the second drive, whereby an open control loop can be applied to the operation of the first and second drives.

Furthermore, in accordance with some preferred embodiments of the present invention, the two geared rollers are connected to a linear position sensor, whereby the actual movement of the elongated device is measured, whereby a closed control loop comprising the actual position of the elongated device from the linear position sensor and the first and second drive positions from the first and second position sensors.

Furthermore, in accordance with some preferred embodiments of the present invention; the elongated device is a medical device.

Furthermore, in accordance with some preferred embodiments of the present invention, the elongated device is a guide wire.

Furthermore, in accordance with some preferred embodiments of the present invention, the elongated device is a catheter.

Furthermore, in accordance with some preferred embodiments of the present invention, there is provided a transmission apparatus for imparting linear, rotary, or combined linear and rotary motion to an elongated device, the apparatus comprising:

a main gear rotationally attached to a support and capable of being driven by a first drive;

a linear drive in which the elongated device may be engaged along an axis of the elongated device's rotation, the linear drive coupled to the first main gear, such that when the first main gear is rotated, the elongated device is rotated about the elongated device's axis of rotation, the linear drive being geared to a second drive to impart linear motion to the elongated device.

Furthermore, in accordance with some preferred embodiments of the present invention, the first drive and the second drive are motors.

Furthermore, in accordance with some preferred embodiments of the present invention, the main gear is provided with a slot to enable lateral insertion or removal of the elongated device.

Furthermore, in accordance with some preferred embodiments of the present invention, the first drive and the second drive are provided with a position tracking mechanism so as to allow automated alignment of the slot and the linear drive for insertion or removal of the elongated device.

Furthermore, in accordance with some preferred embodiments of the present invention, the linear drive comprises two geared rollers.

Furthermore, in accordance with some preferred embodiments of the present invention, the two geared rollers resiliently grip the elongated device, and may be separated in order to insert or remove the elongated device.

Furthermore, in accordance with some preferred embodiments of the present invention, a first position sensor measures the position of the first drive and a second position sensor measures the position of the second drive, whereby an open control loop can be applied to the operation of the first and second drives.

Furthermore, in accordance with some preferred embodiments of the present invention, the two geared rollers are connected to a linear position sensor, whereby the actual movement of the elongated device is measured, whereby a closed control loop comprising the actual position of the elongated device from the linear position sensor and the first and second drive positions from the first and second position sensors.

Furthermore, in accordance with some preferred embodiments of the present invention, the first drive comprises a motor that imparts rotational force to a first drive roller that both imparts rotational force to the main gear and imparts rotational force via a translation roller to a second drive roller that also imparts force to the main gear.

Furthermore, in accordance with some preferred embodiments of the present invention, the second drive is a motor that is driven by an internal source and controlled via wireless means.

Furthermore, in accordance with some preferred embodiments of the present invention, the second drive is a that is driven by power from a coil on the main gear that is in contact with brushes on the base.

Furthermore, in accordance with some preferred embodiments of the present invention, the elongated device is a medical device.

Furthermore, in accordance with some preferred embodiments of the present invention, the elongated device is a guide wire.

Furthermore, in accordance with some preferred embodiments of the present invention, the elongated device is a catheter.

Furthermore, in accordance with some preferred embodiments of the present invention, there is provided a method for imparting linear, rotary, or combined linear and rotary motion to an elongated device, the method comprising:
   rotating a first main gear rotationally attached to a support and capable of being driven by a first drive;
   rotating a second main gear coaxially and rotationally attached to the first main gear, the second main gear geared to a roller drive gear and capable of being driven by a second drive;
   engaging the elongated device along an axis of the elongated device's rotation in a linear drive, the linear drive coupled to the first main gear, such that when the first main gear is rotated, the elongated device is rotated about the elongated device's axis of rotation, the linear drive being geared to the roller drive gear, such that when the second main gear is rotated the linear drive imparts linear motion to the elongated device.

Furthermore, in accordance with some preferred embodiments of the present invention, there is provided a method for imparting linear, rotary, or combined linear and rotary motion to an elongated device, the method comprising:
   rotating a main gear rotationally attached to a support and capable of being driven by a first drive;

engaging the elongated device along an axis of the elongated device's rotation in a linear drive, the linear drive coupled to the main gear, such that when the main gear is rotated, the elongated device is rotated about the elongated device's axis of rotation, the linear drive being geared to a second drive, such that the linear drive imparts linear motion to the elongated device.

BRIEF DESCRIPTION OF THE FIGURES

The invention is described herein, by way of example only, with reference to the accompanying Figures, in which like components are designated by like reference numerals.

DETAILED DESCRIPTION OF THE INVENTION

The present invention discloses a transmission apparatus for imparting motion from at least one of a plurality of motion sources into linear, rotary, or combined linear and rotary motion of an elongated device.

A preferred embodiment of the present invention provides a mechanical transmission for a remote control catheterization system, such as that of U.S. Pat. No. 6,726,675 REMOTE CONTROL CATHETERIZATION (2004), Dalia Beyar, which is included herein by reference. The innovation of the present invention is the transmission that it provides. While the present invention is particularly suited for integration with U.S. Pat. No. 6,726,675, it can generally be used with other remote control catheterization systems for linear and rotational motion of a guide wire or catheter. Furthermore, it can be integrated into any system that incorporates user-determined motion of an elongated device along or around the device's longitudinal axis. In a preferred embodiment of the present invention, the elongated device is a guide wire, however it could equally be another type of elongated device, such as a catheter or probe.

Figure 1:
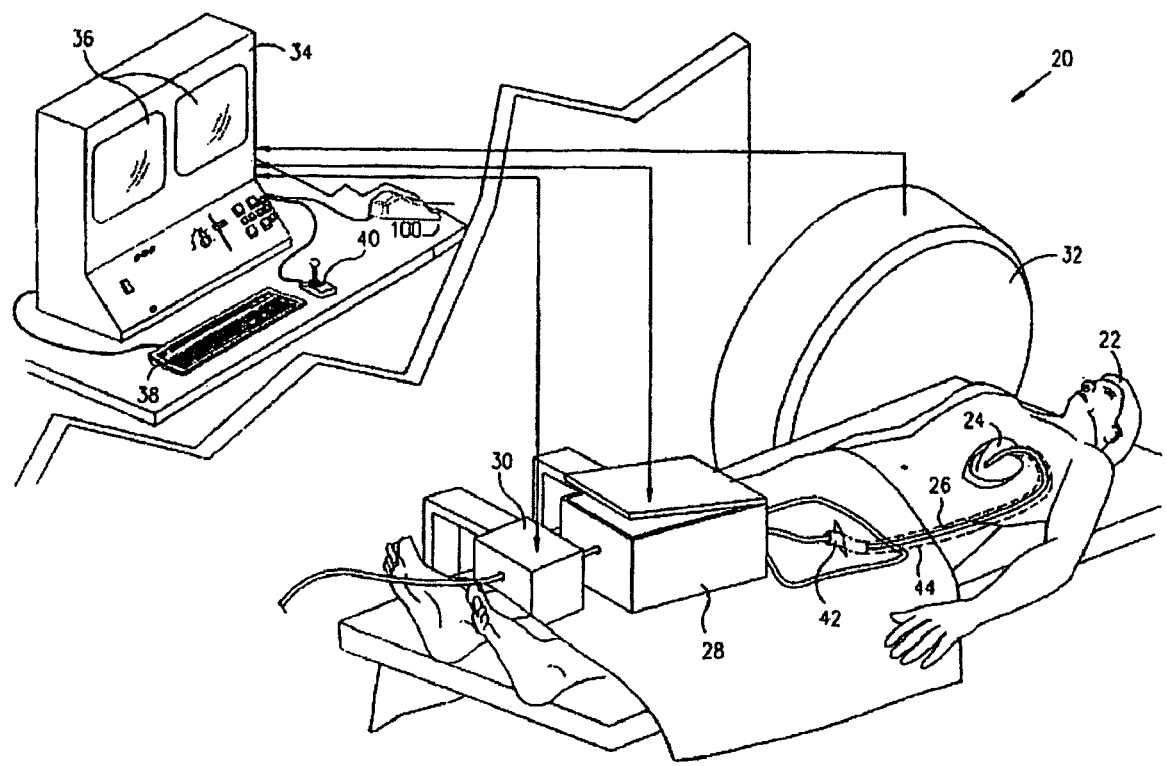
FIG. 1 is a view of a remote control catheterization system incorporating a mechanical transmission, in accordance with a preferred embodiment of the present invention.

Reference is now made to FIG. 1, which is a simplified, pictorial illustration of a remote control catheterization system 20, in accordance with a preferred embodiment of the present invention. The invention of U.S. Pat. No. 6,726,675 is summarized as follows:

System 20 comprises a guiding catheter (or guide wire, other elongated probe, or other elongated device) 26, which is fed via a cannula 42 into a blood vessel 44 leading to a target location in a vessel or a heart 24 of a patient 22.

Preferably, the catheter is fed over a guide wire, which is omitted in FIG. 1 for simplicity.

Catheter 26 is fed through a catheter propelling device 28, and then coupled proximally with a catheter interface 30.

Interface 30 may be used to perform various therapeutic and/or diagnostic catheter procedures, such as balloon inflation or injection of contrast media, or any other such catheter-based treatments known in the art. A fluoroscope 32 is used to capture images showing the position of catheter 26 in the patient's body. (For simplicity, the X-ray tube associated with the fluoroscope is not shown in the figure.) Propelling device 28, interface 30 and fluoroscope 32 all communicate with a control unit 34. The various elements of system 20 relay operative information to console 34, and receive operative instructions from the console. Preferably, device 28 relays to console 34 force measurements associated with insertion of the catheter and an indication of the distance that the catheter has traveled; interface 30 relays applicable data from the catheter regarding the therapeutic and/or diagnostic procedures being performed; and fluoroscope 32 conveys X-ray images.

The data are preferably displayed on console 34 via a pair of displays, monitors 36. Preferably, one of monitors 36 displays fluoroscopic images, and the other monitor displays data received from propelling device 28 and interface 30.

Alternatively, the data may be presented using dials, meters, or any means known and used in the art.

Medical personnel operating system 20 use device 38, preferably a keyboard, to send directional commands, for example to control table and fluoroscope motions, and to operate interface 30 and fluoroscope 32. A user interface device 40, preferably a handle, is moved by a user to initiate linear or rotational movement. The direction and distance of the move is relayed via circuitry to propelling device 28. While the user of the present invention is assumed to be a medical professional, the invention can be easily adapted by one skilled in the art, for an automated user, such as a mechanical, electrical, or optical mechanism.

In order to prevent exposure by medical staff to the fluoroscope's high levels of radiation, console 34 is preferably located outside of the catheterization room or in an area of the room that is shielded from radiation generated by the fluoroscope X-ray tube. The present invention, via this usage of remote control communication with console 34, thus furnishes the medical staff with all the relevant information, and all the relevant remote control means, to perform the catheterization operation without danger of radiation exposure.

Alternatively or additionally, console 34, or certain elements thereof, may be in a remote location, even in a different city from the patient, and communicate with the other elements of system 20 over telecommunication channels. As noted above with reference to FIG. 1, cannula 42 is inserted into blood vessel 44. Preferably a guide wire is threaded through cannula 42 into vessel 44. Once the guide wire is in a desired position, catheter 26 is slipped over the guide wire and guided to a desired position, for example, in one of the chambers of heart 24 or in one of the coronary arteries.

Once catheter 26 is in place, the guide wire may be withdrawn if desired. An ancillary instrument (not shown), such as an angioplasty balloon, may be passed through the catheter, into the heart or arteries. The guide wire, catheter and ancillary instrument are themselves substantially similar to devices of these types known in the art.

The mechanical transmission 100 of the present invention forms part of propelling device 28, converting motor motion into linear, rotational, or combined linear and rotational motion of the guide wire.

Transmission 100 can be implemented many ways, as will be clear to one skilled in the art. Herein a preferred embodiment of transmission 100 is described to illustrate one implementation.

Figure 2:
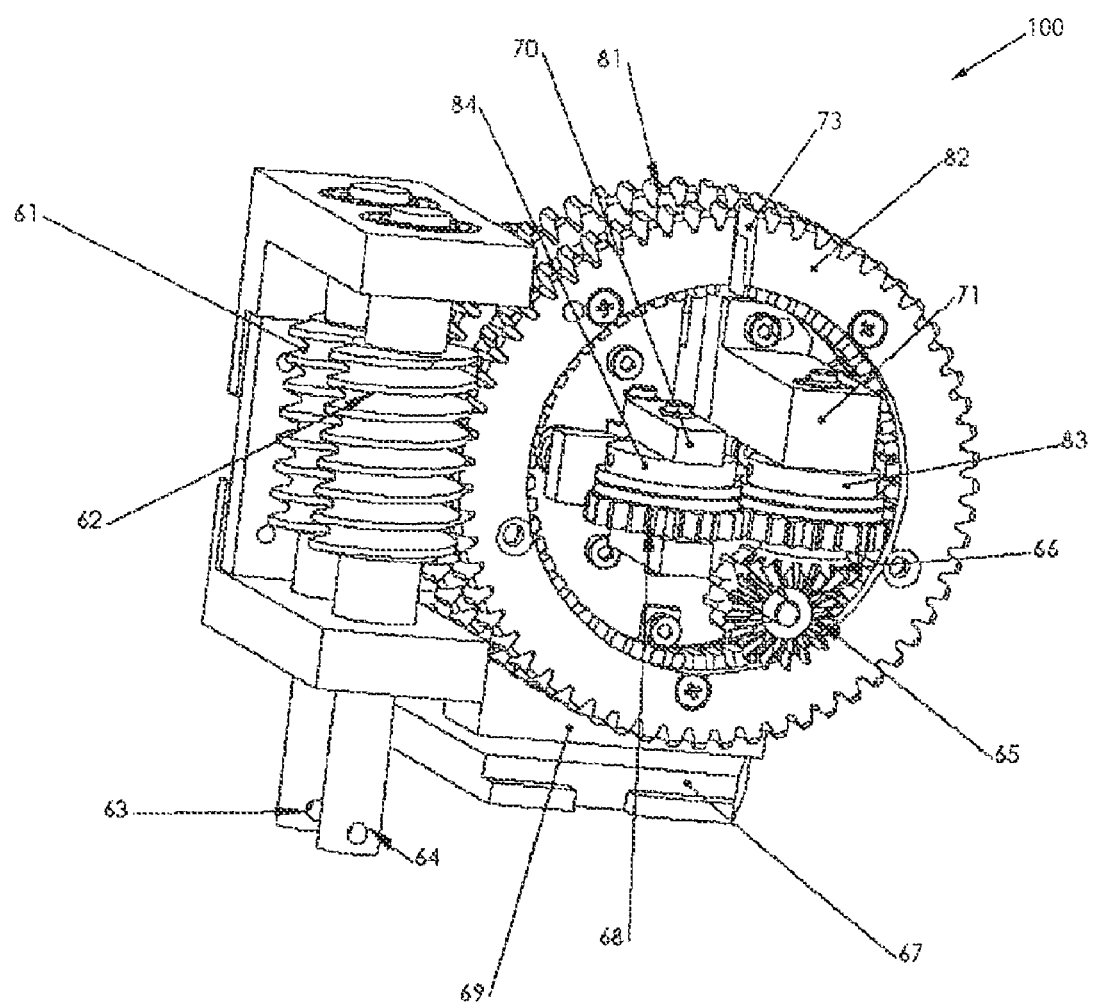
FIG. 2 is a front projection view of a mechanical transmission, in accordance with a preferred embodiment of the present invention.
Figure 3:
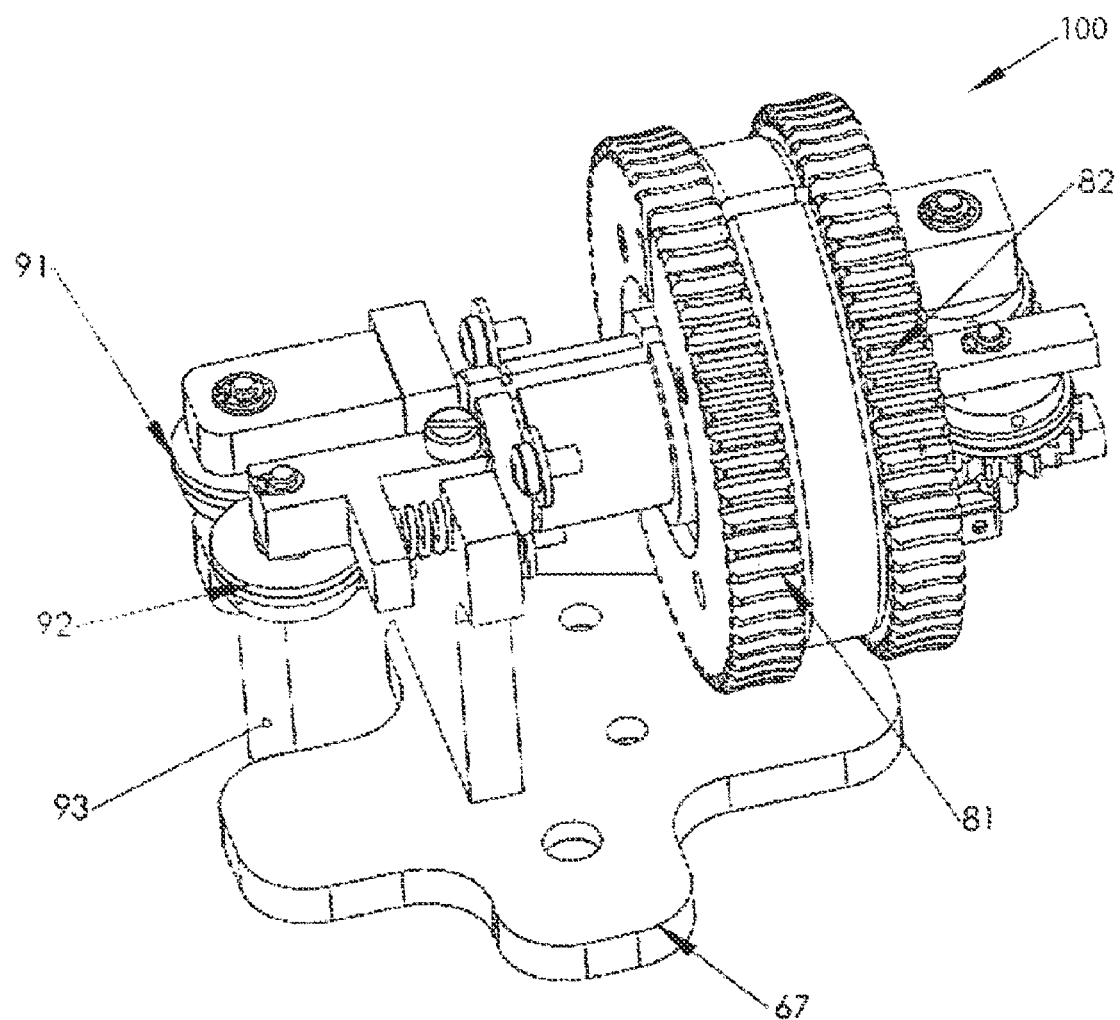
FIG. 3 is a top projection view of a mechanical transmission, in accordance with a preferred embodiment of the present invention.

The components of a preferred embodiment of transmission 100 are now described with reference to FIG. 2 and FIG. 3.

Transmission mechanism 100 is composed of a set of rotating parts and some stationary parts that can move the guide wire when driven by two motors. The combined motion of the motors causes motion of the guide wire linearly, rotationally, or both. The guide wire is held between two rollers and moved linearly by rotation of the rollers and rotationally by rotation of the base of the rollers.

Transmission mechanism 100 essentially consists of a turret assembly, a base to hold the turret, and two gears to pass motion from the motors to the turret.

The turret comprises two large (relative to the smaller gears mounted inside them) diameter gears, where first main gear 81 is attached via a cylindrical bush to base 67 in a manner that permits rotational movement of first main gear 81 and second main gear 82 is attached to first main gear 81 in a manner that permits rotational movement of part 82 independent of first main gear 81.

First main gear 81 has teeth on its outer perimeter to accept motor force from drive screw 61. Drive Screw 61 is turned by drive shaft 63, which is turned by a motor (not shown). An encoder or other position sensor can be installed on the motor or the drive screw 61.

First main gear 81 has a slot, similar to slot 73 of gear 82, in its perimeter to facilitate insertion of the guide wire between rollers 83 and 84 from the side. The slot enables insertion of the guide wire at any time directly through the slot and between rollers 83 and 84, thereby eliminating the need to insert the end of the guide wire and feed it through until reaching the desired point on the guide wire at which to apply the rollers. Similarly the slot enables direct removal of the guide wire instead of having to pull the entire length of the wire through the rollers.

Second main gear 82 has teeth on its outer perimeter as well as on its inner perimeter and is mounted on first main gear 81 such that it can rotate independently and coaxially to first main gear 81. Second main gear 82 transmits forces from drive screw 62 to roller drive gear 65. Drive screw 62 is turned by drive shaft 64, which is turned by a motor (not shown). An encoder or other position sensor can be installed on the motor or on drive screw 62.

Like first main gear 81, second main gear 82 has a slot 73 to facilitate the insertion of the guide wire directly into the rollers 83 and 84 from the side, thereby removing the need to feed the length of the guide wire into the rollers.

To use the slots in gears 81 and 82 for these purposes, the operator activates a control on console 34. The system already knows the position of the slots from feedback from the encoders on the motors or drive screws. The system calculates the closest point where the slots can be aligned and commands the motor to move them into alignment. The guide wire can then be inserted/removed between/from rollers 83 and 84 via the slots.

Rollers 83 and 84 hold the guide wire and drive it linearly, by translating mechanical energy received through the transmission from the motors. Drive roller 83 is driven by roller gear 65, which is driven by second main gear 82. This motion moves the guide wire longitudinally and, according to the direction of rotation, inserts the guide wire into the patient or retracts the guide wire from the patient.

Holder roller 84 holds the guide wire against part 83 and is mounted on movable holder arm 70 in a manner that governs the pressure between holder roller 84 and drive roller 83 such that the guide wire is held firmly without slipping. In a preferred embodiment of the present invention, this is effected by spring-loading arm 70. Holder roller 84 receives motion from drive roller 83, thereby ensuring that holder roller 84 rotates at the same speed as drive roller 83.

Both drive roller 83 and holder roller 84 are mounted indirectly on first main gear 81. Therefore, when first main gear 81 rotates behind second main gear 82, the bases of rollers (83 and 84) are rotated correspondingly, imparting rotational movement to the guide wire held by the rollers. This results in rotational guide wire motion similar to that an operator imparts with his fingers when driving the guide wire manually.

When second main gear 82 rotates on first main gear 81, rollers 83 and 84 rotate about their axes and impart linear motion to the guide wire. This results in longitudinal guide wire motion similar to the linear movement that an operator imparts with his hand when driving the guide wire manually.

The primary purpose of transmission 100 is to translate motor motion to linear and/or rotational motion of the guide wire. In the preferred embodiment described here this is accomplished as follows:

linear motion only: rotation of front main gear 82 only
rotational motion only: rotation of both main gears, 81 and 82, in the same direction
linear and rotational motion.

Combined movement of main gears 81 and 82 each relative to the other results in the desired motion.

In equation form, vectors (V) of movement for main gears 81 and 82 are as follows:

$$V\text{linear}=V(81)+V(82)$$

$$V\text{rotation}=V(81)$$

For linear movement only, Vrotation=0, therefore V(81)=0, therefore Vlinear=V(82)

For rotational movement only, Vrotation=V(81)

For combined linear and rotational movement, since Vrotation=V(81), therefore V(82)=Vlinear−V(81), Once the required linear speed (Vlinear) and rotation speed (Vrotation=V81), then V(82) is known.

Position translation rollers 91 and 92 are rollers that are free to rotate about their axes, holding the guide wire between them with sufficient pressure that longitudinal movement of the guide wire causes a corresponding rotation of the rollers. The rotation of the rollers is measured by an encoder, or other position sensor, connected to shaft 93. Shaft 93 is common for both the encoder and position translation roller 91. Therefore the encoder measures the movement of position translation roller 91 and, thereby, the linear movement of the guide wire. For purposes of closing a control loop, the actual linear movement of the guide wire measured by the encoder attached to shaft 93 can be compared with the motor movements measured by the encoders attached to the motors or to the drive screws 61 and 62.

If the actual position of the guide wire measured by the encoder connected to Shaft 93 is different from that expected from the movement of the motors, it indicates that the guide wire is encountering obstacles. Various system reactions to this condition can be programmed, for example, stop movement of the guide wire, retract the guide wire, generate some type of alarm, etc.

Figure 4:
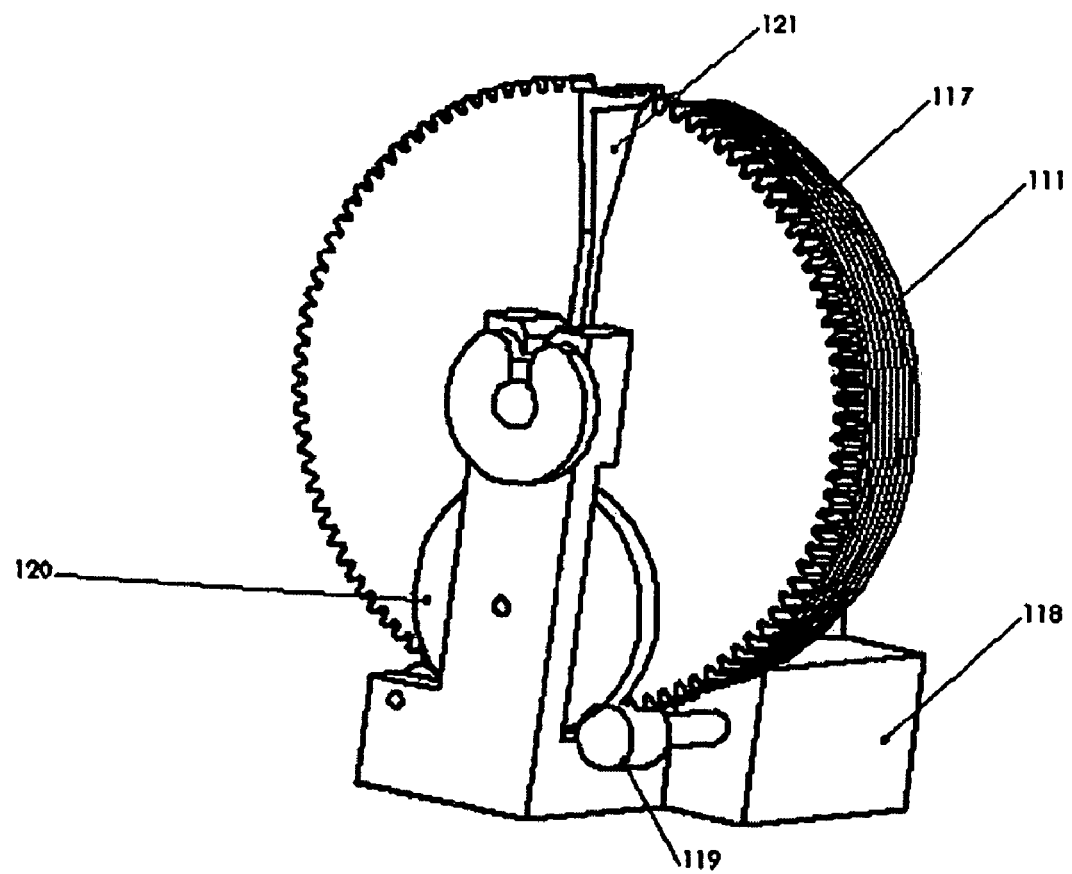
FIG. 4 is a rear projection view of a mechanical transmission, in accordance with another preferred embodiment of the present invention.
Figure 5:
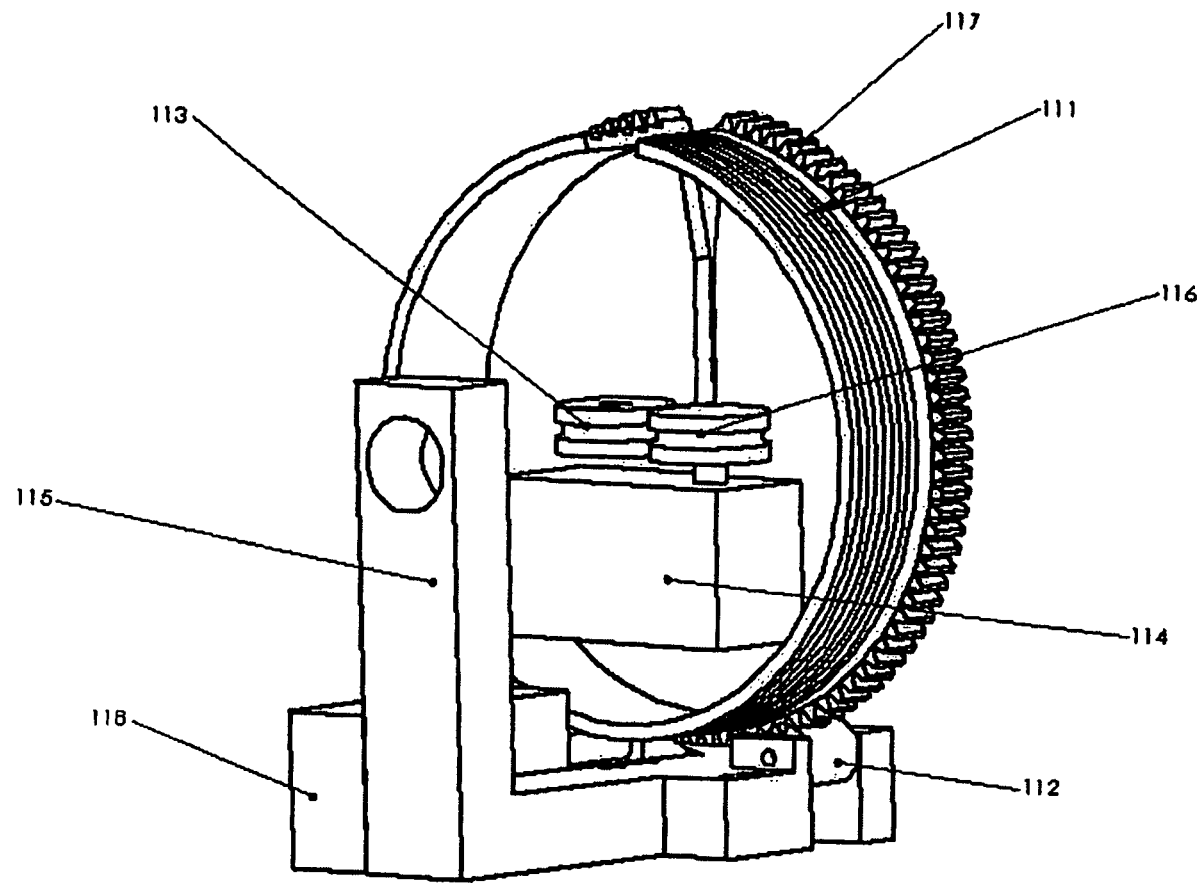
FIG. 5 is a front projection view of a mechanical transmission, in accordance with another preferred embodiment of the present invention.

Another preferred embodiment of the present invention is detailed in FIG. 4 and FIG. 5. In this embodiment, the turret comprises a main gear 117 mounted on base 115 and geared on its outer perimeter to accept motor force from drive rollers 119 and 112. First drive roller 119 is turned by motor 118 and rotates second drive roller 112 via wheel 120. Main gear 117 has a slot 121 in its perimeter to facilitate insertion of the guide wire between linear drive rollers 113 and 116 from the side. The slot enables insertion of the guide wire at any time directly through the slot and between linear drive rollers 113 and 116, thereby eliminating the need to insert the end of the guide wire and feed it through until reaching the desired point on the guide wire at which to apply the rollers. Similarly the slot enables direct removal of the guide wire instead of having to pull the entire length of the wire through the rollers.

Linear drive rollers 113 and 116 hold the guide wire and drive it linearly, by translating mechanical energy received through motor 114. The rollers are mounted on main gear 117 such that when main gear 117 rotates, the assembly comprising the rollers rotates with it.

Motor 114 receive its power in a manner that enables controlled transmission of power while leaving the motor free to rotate with main gear 117. There are several ways to accomplish this. For example, the motor can be powered by a self-contained source, such as an internal battery, or through electrical circuit 111. Circuit 111 is an open circuit implemented as a coil on main gear 117 that is movably in contact with brushes located on base 115. Control of the motor can be implemented via a wireless means (such as infra red communication) in the case of a self-contained source or via the coil in electrical circuit 111 in the case of that implementation.

Linear movement of the guide wire is accomplished by motor 114 rotating the rollers 113 and 116 only.

Rotational movement of the guide wire is accomplished by motor 118 moving main gear 117. This rotates the assembly comprising rollers 113 and 116, thereby rotating the guide wire.

Combined linear and rotational movement of the guide wire can be done by combining movement of both motors, each controlled independent of the other.

Position of the motors and of the guide wire can be tracked by position sensors as was described earlier in this disclosure.

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

The invention claimed is:

1. A transmission apparatus comprising:
a first main gear rotationally attached to a support and capable of being driven by a first drive;
a second main gear being coaxial to the first main gear and rotationally attached to the first main gear, the second main gear geared to a roller drive gear and being driven by a second drive;
a linear drive in which an elongated device is engaged along an axis of rotation of the elongated device, the linear drive coupled to the first main gear, when the first main gear is rotated, the elongated device is rotated about the elongated device's axis of rotation, the linear drive being geared to the roller drive gear, when the second main gear is rotated the linear drive imparts linear motion to the elongated device; and
the first main gear including a first slot extending from an outer perimeter of the first main gear to the center of the first main gear and the second main gear including a second slot extending from an outer perimeter of the second main gear to the center of the second main gear, the first and second slots being aligned in a common plane in a first position, the elongated device being removably received into the linear drive through the first slot and second slot when the first and second gears are in the first position.

2. The apparatus of claim 1, wherein the first drive and the second drive transmit power to the first main gear and the second main gear respectively via drive screws.

3. The apparatus of claim 1, wherein the first drive and the second drive are motors.

4. The apparatus of claim 1, further comprising a position sensor configured to allow automated alignment of the slots for insertion or removal of the elongated device.

5. The apparatus of claim 1, wherein the linear drive comprises two geared rollers that are geared to the second main gear.

6. The apparatus of claim 5, wherein the two geared rollers resiliently grip the elongated device, and may be separated in order to insert or remove the elongated device.

7. The apparatus of claim 6, wherein the two geared rollers are connected to a linear position sensor, whereby the actual movement of the elongated device is measured, whereby a closed control loop comprising the actual position of the elongated device from the linear position sensor and the first and second drive positions from the first and second position sensors.

8. The apparatus of claim 1, wherein a first position sensor measures the position of the first drive and a second position sensor measures the position of the second drive, whereby an open control loop can be applied to the operation of the first and second drives.

9. The apparatus of claim 1 wherein the elongated device is a medical device.

10. The apparatus of claim 1 wherein the elongated device is a guide wire.

11. The apparatus of claim 1 wherein the elongated device is a catheter.

12. A transmission for an elongated device having a first end, a second opposing end and a length intermediate the first and second ends, the transmission comprising:
 a first main gear having an outer perimeter and a slot extending from the outer perimeter to a center of the first main gear, the slot configured to permit passage of the elongated device from the outer perimeter of the first main gear to the center of the first main gear;
 a first roller wheel and a second roller wheel coupled to a housing being secured to the first main gear, the first roller wheel and second roller wheel configured to receive a portion of the elongated device therebetween; and
 wherein, rotation of the first main gear rotates the housing and first and second roller wheels about a rotational axis of the elongated device, the rotational axis extending through the center of the first main gear and being substantially perpendicular to the first main gear.

13. The transmission for an elongated device of claim 12, further including a support supporting the first main gear, the support having an outer perimeter and a slot extending from the outer perimeter therein, the slot configured to permit passage of the elongated device from the outer periphery of the support to the rotational axis.

14. The transmission for an elongated device of claim 13, wherein the roller wheels are movable toward and away from each other to facilitate insertion and removal of the elongated device.

15. The transmission for an elongated device of claim 14, wherein the roller wheels and first main gear are movable to a first position where a gap between the roller wheels and the slots in the support and first main gear are all aligned to permit insertion and removal of the elongated device.

16. The transmission for an elongated device of claim 15 wherein the elongated device is one of a guidewire and catheter device.

17. The transmission for an elongated device of claim 16 wherein the first main gear includes a plurality of gear teeth proximate the perimeter of the first main gear.

18. The transmission for an elongated device of claim 16 further including a position tracking mechanism to allow automated alignment of the slot for insertion or removal of the elongated device between the rollers.

19. A method for rotating an elongated device having a first end, a second opposing end, the method comprising:
 providing a transmission having a first main gear including an outer perimeter and a slot extending from the outer perimeter to a center of the first main gear,
 providing a first roller and a second roller coupled to a housing being secured to the first main gear,
 providing a position tracking mechanism to allow automated alignment of the slot for insertion or removal of the elongated device between the rollers,
 automatically aligning the slot in the first main gear and the gap between the first roller and second roller with the position tracking mechanism and placing a length of the elongated device intermediate the first and second ends through the slot in the first main gear and between the first roller and second roller such that the elongated device extends through the center of the first main gear and between the first and second rollers,
 rotating the elongated device about its axis of rotation by rotating the first main gear and first and second rollers and the housing about the axis of rotation of the elongated device, where the rotational axis of the elongated device is perpendicular to the first main gear.

20. A method comprising:
 rotating a first main gear rotationally attached to a support and capable of being driven by a first drive, the first main gear having a first slot extending from an outer perimeter of the first main gear to a center of the first main gear;
 rotating a second main gear being coaxial to the first main gear and rotationally attached to the first main gear, the second main gear geared to a roller drive gear and being driven by a second drive, the second main gear having a second slot extending from an outer perimeter of the second main gear to a center of the second main gear;
 moving a portion of an elongated device through the first and second slots from the outer perimeter of the first and second main gears to the center of the first and second main gears; and
 engaging the elongated device along an axis of rotation of the elongated device in a linear drive, the linear drive coupled to the first main gear, such that when the first main gear is rotated, the elongated device is rotated about the elongated device's axis of rotation, the linear drive being geared to the roller drive gear, such that when the second main gear is rotated the linear drive imparts linear motion to the elongated device.

* * * * *